(12) United States Patent
Pinter et al.

(10) Patent No.: US 12,142,351 B2
(45) Date of Patent: Nov. 12, 2024

(54) ENHANCED DIAGNOSTICS FOR A TELEPRESENCE ROBOT

(71) Applicant: INTOUCH TECHNOLOGIES, INC., Goleta, CA (US)

(72) Inventors: Marco Pinter, Santa Barbara, CA (US); Timothy C. Wright, Santa Barbara, CA (US); H. Neal Reynolds, Severna Park, MD (US); Fuji Lai, Goleta, CA (US); Yulun Wang, Goleta, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

(21) Appl. No.: 15/985,448

(22) Filed: May 21, 2018

(65) Prior Publication Data
US 2018/0263703 A1    Sep. 20, 2018

Related U.S. Application Data

(63) Continuation of application No. 14/091,292, filed on Feb. 13, 2014, now Pat. No. 9,974,612, which is a
(Continued)

(51) Int. Cl.
*A61B 34/10*    (2016.01)
*A61B 5/00*    (2006.01)
(Continued)

(52) U.S. Cl.
CPC .......... *G16H 10/60* (2018.01); *A61B 5/0008* (2013.01); *A61B 5/0013* (2013.01);
(Continued)

(58) Field of Classification Search
CPC ....... A61B 34/10; A61B 34/30; A61B 5/0008; A61B 5/746; A61B 5/0013; A61B 5/0022;
(Continued)

(56) References Cited

U.S. PATENT DOCUMENTS

2004/0064080 A1 * 4/2004 Cruz ................. A61M 1/16
                                                         604/5.04
2005/0027400 A1 * 2/2005 Wang ............... B25J 9/1689
                                                         700/259
(Continued)

FOREIGN PATENT DOCUMENTS

CN        1804559 A   *  7/2006
JP     2003319357 A   * 11/2003

OTHER PUBLICATIONS

Wu et al., Eulerian Video Magnification for Revealing Subtle Changes in the World, ACM Transactions on Graphics/Siggraph 2012 Conference Proceedings, vol. 31, No. 4, Jul. 2012 (Year: 2012).*

(Continued)

*Primary Examiner* — Yuen Wong

(57) ABSTRACT

A telepresence device may autonomously check patients. The telepresence device may determine the frequency of checking based on whether the patient has a risk factor. The telepresence device may include an image sensor, a thermal camera, a depth sensor, one or more systems for interacting with patients, or the like. The telepresence device may be configured to evaluate the patient's condition using the one or more sensors. The telepresence device may measure physiological characteristics using Eulerian video magnification, may detect pallor, fluid level, or fluid color, may detect thermal asymmetry, may determine a psychological state from body position or movement, or the like. The telepresence device may determine whether the patient is experiencing a potentially harmful condition, such as sepsis or stroke, and may trigger an alarm if so. To overcome alarm fatigue, the telepresence device may annoy a care provider until the care provider responds to an alarm.

7 Claims, 12 Drawing Sheets

Related U.S. Application Data continuation of application No. 14/108,036, filed on Dec. 16, 2013, now abandoned, which is a continuation-in-part of application No. 13/830,334, filed on Mar. 14, 2013, now Pat. No. 9,098,611, and a continuation-in-part of application No. 13/111,208, filed on May 19, 2011.

(60) Provisional application No. 61/729,964, filed on Nov. 26, 2012.

(51) Int. Cl.
| | |
|---|---|
| *A61B 5/01* | (2006.01) |
| *A61B 5/0205* | (2006.01) |
| *A61B 5/11* | (2006.01) |
| *A61B 5/16* | (2006.01) |
| *A61B 34/30* | (2016.01) |
| *B25J 9/16* | (2006.01) |
| *B25J 11/00* | (2006.01) |
| *G05D 1/00* | (2006.01) |
| *G16H 10/60* | (2018.01) |
| *G16H 40/67* | (2018.01) |
| *G16H 50/20* | (2018.01) |
| *H04N 7/14* | (2006.01) |
| *A61B 5/024* | (2006.01) |

(52) U.S. Cl.
CPC .......... *A61B 5/0022* (2013.01); *A61B 5/0075* (2013.01); *A61B 5/0077* (2013.01); *A61B 5/015* (2013.01); *A61B 5/02055* (2013.01); *A61B 5/1128* (2013.01); *A61B 5/165* (2013.01); *A61B 5/4064* (2013.01); *A61B 5/4809* (2013.01); *A61B 5/7264* (2013.01); *A61B 5/7275* (2013.01); *A61B 5/741* (2013.01); *A61B 5/742* (2013.01); *A61B 5/746* (2013.01); *A61B 34/10* (2016.02); *A61B 34/30* (2016.02); *B25J 9/1689* (2013.01); *B25J 11/009* (2013.01); *G05D 1/0038* (2013.01); *G16H 40/67* (2018.01); *G16H 50/20* (2018.01); *H04N 7/148* (2013.01); *A61B 5/024* (2013.01)

(58) Field of Classification Search
CPC ..... A61B 5/0075; A61B 5/0077; A61B 5/015; A61B 5/02055; A61B 5/1128; A61B 5/165; A61B 5/4064; A61B 5/4809; A61B 5/7264; A61B 5/7275; A61B 5/741; A61B 5/742; A61B 5/024; G16H 50/20; G16H 40/67; G06F 19/3418; G05D 1/0038; G05D 2201/0206; B25J 11/009; B25J 9/1689; H04N 7/148

See application file for complete search history.

(56) References Cited

U.S. PATENT DOCUMENTS

| | | | | |
|---|---|---|---|---|
| 2005/0225448 | A1* | 10/2005 | Schenker | G08B 21/22 340/573.1 |
| 2009/0089100 | A1* | 4/2009 | Nenov | G16H 20/10 705/3 |
| 2011/0288417 | A1* | 11/2011 | Pinter | A61B 5/0033 600/473 |

OTHER PUBLICATIONS

Kakii_JP2003319357A_machine translation by EPO and Google (Year: 2003).*

Li_CN1804559A_machine translation by EPO and Google (Year: 2006).*

* cited by examiner ations Ser. No. 14/091,292, filed Feb. 13, 2014, which is a
ENHANCED DIAGNOSTICS FOR A TELEPRESENCE ROBOT

RELATED APPLICATIONS

This application is a continuation of U.S. patent application Ser. No. 14/091,292, filed Feb. 13, 2014, which is a continuation of U.S. patent application Ser. No. 14/108,036, filed Dec. 13, 2013, which claims priority to U.S. Patent Application Ser. No. 61/729,964 filed Nov. 26, 2012 and entitled "Enhanced Diagnostics Using Multiple Sensors with Coordinated Sensor Spaces" and is a continuation-in-part of U.S. patent application Ser. No. 13/111,208, filed May 19, 2011 and entitled "Mobile Videoconferencing Robot System with Autonomy and Image Analysis" and a continuation-in-part of U.S. patent application Ser. No. 13/830,334 filed Mar. 14, 2013 and entitled "Enhanced Video Interaction for a User Interface of a Telepresence Network," all of which are hereby incorporated by reference herein in their entirety.

STATEMENT REGARDING FEDERALLY SPONSORED RESEARCH OR DEVELOPMENT

This invention was made with government support under grant number R43 MD006709.

TECHNICAL FIELD

This disclosure relates to enhanced diagnostics for a telepresence device. More specifically, this disclosure relates to systems and methods for improving patient diagnosis by a telepresence device configured to autonomously check patients.

BRIEF DESCRIPTION OF THE DRAWINGS

Non-limiting and non-exhaustive embodiments of the disclosure are described herein, including various embodiments of the disclosure illustrated in the figures listed below.

Figure 1:
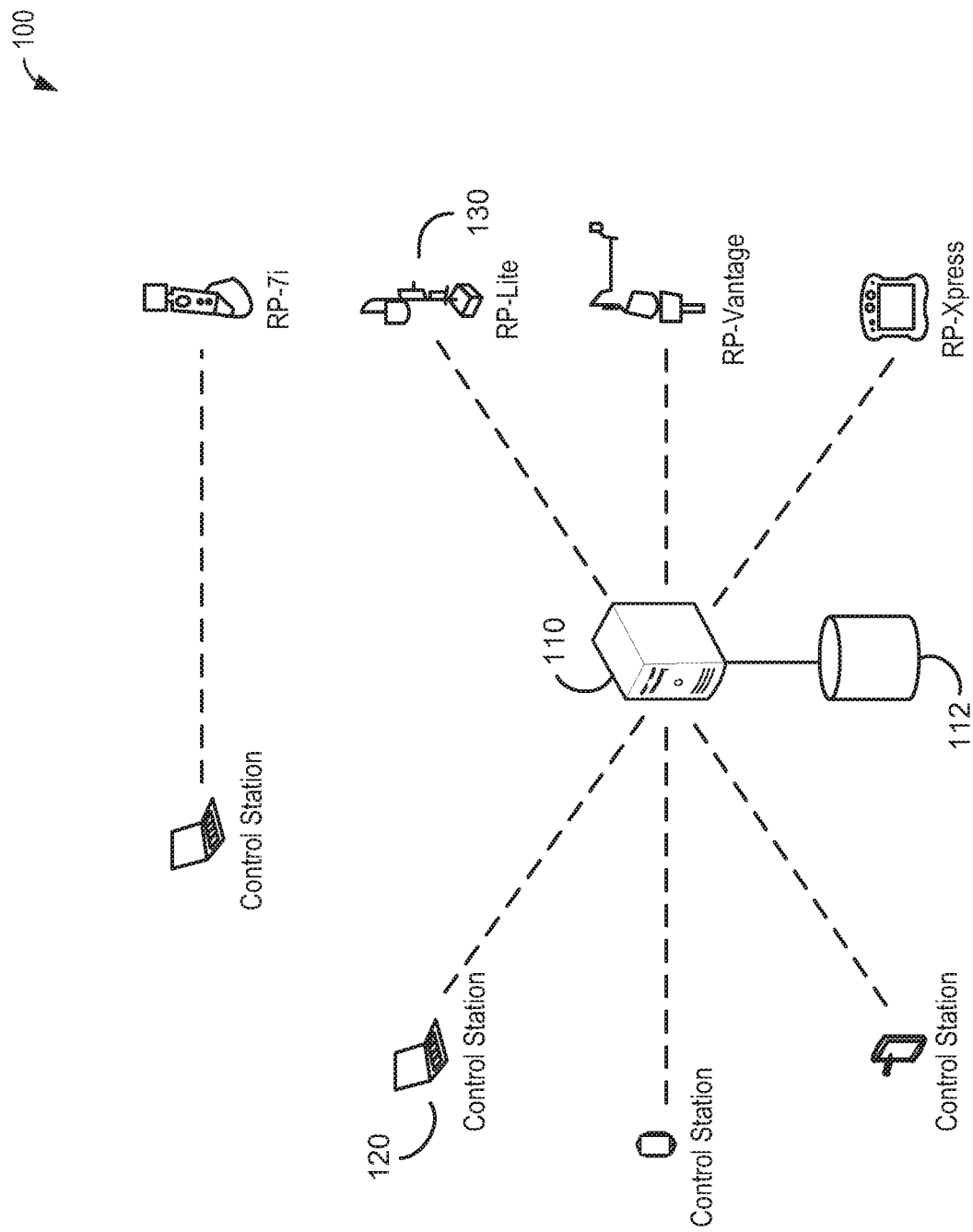
FIG. 1 is a schematic diagram of a telepresence network comprising a plurality of telepresence devices.

The described features, structures, and/or characteristics of the systems and methods described herein may be combined in any suitable manner in one or more alternative embodiments, and may differ from the illustrated embodiments.

DETAILED DESCRIPTION OF PREFERRED EMBODIMENTS

In certain industries, a shortage of skilled employees may result in poor outcomes, particularly during night shifts when skilled employees are less likely to be working. For example, the difficulties with filling night shifts may be especially pervasive in hospitals, such as hospitals in underserved urban communities, in high-crime neighborhoods, and/or in rural areas where specialists are unavailable and local caregivers do not recognize the need for remote specialists. Less skilled employees may be used to fill the shortage, but they often require additional supervision and may perform more poorly than their high-skill counterparts, which may result in higher mortality rates in hospitals, for example. Hospitals may require that patients at risk for specific diseases be checked at predetermined intervals, but low-skilled employees may be less consistent in how they check patients and may neglect to check patients until the end of their shifts, which may be too late. Accordingly, there is a strong need to address the problems of availability, quality, and reliability of nighttime healthcare in disadvantaged communities.

A telepresence device may be part of a telepresence network that allows users remote from the telepresence device to interact with an environment where the telepresence device is located. When no remote users are interacting with the telepresence device, it may act autonomously. For example, the telepresence device may automatically perform rounds and check on patients with a predetermined frequency (e.g., at predetermined intervals). The telepresence device may be configured to capture video and/or environmental measurements, which may be relayed to one or more users and/or stored for later viewing. The telepresence device may also, or instead, detect the existence of problems based on the captured video and/or environmental measurements and may alert one or more users of the problem. A control device may allow the one or more users to interact with the telepresence device, such as by sending and/or receiving captured video and/or audio, sending commands to the telepresence device, and the like. The telepresence device may be more reliable in complying with strict patient monitoring schedules and may provide a consistent level of care with each visit.

Each telepresence network may include one or more facilities that each include at least one corresponding telepresence device local to the facility. Exemplary facilities may include manufacturing plants, research and development facilities, testing facilities, hospitals, rehabilitation facilities, long-term care facilities, and the like. Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations.

Exemplary, non-limiting uses for telepresence devices may include healthcare and industrial applications. For example, healthcare facilities may include telemedicine technologies, such as telepresence devices in a telepresence network, that allow remote healthcare practitioners to provide services to patients and/or other healthcare practitioners in remote locations. A remote medical professional may be a neurologist practicing in a relatively large hospital who may, via a telepresence device, provide services and consultations to patients and/or other medical professionals in hospitals located in rural areas that otherwise may not have a neurologist on staff.

The control device may include a general purpose and/or special purpose computer systems and/or one or more computer networks. In an embodiment, the control device and the telepresence device may each include at least one camera, at least one display device, at least one speaker, and at least one microphone to allow for two-way video/audio communication. One or more input devices may allow the user of the control device to remotely control movement of the telepresence device. Additional discussion of remotely controlling movement of a telepresence device is contained in U.S. Pat. No. 6,845,297, titled "Method and System for Remote Control of Mobile Robot," filed on Jan. 9, 2003, and European Patent No. 1279081, titled "Method and System for Remote Control of Mobile Robot," filed on May 1, 2001, which applications are hereby incorporated by reference in their entireties.

The control device, the telepresence device, and/or the telepresence network may be configured to store session content data, such video and/or audio recordings, telemetry data (e.g., physiological data), notes, time stamps, and/or the like. In an embodiment, the telepresence network may include a server configured to store the session content data. Additional discussion of data storage for telepresence devices and automatic use of stored data is contained in U.S. patent application Ser. No. 12/362,454, titled "DOCUMENTATION THROUGH A REMOTE PRESENCE ROBOT," filed on Jan. 29, 2009, which application is hereby incorporated by reference in its entirety.

Reference throughout this specification to "one embodiment" or "an embodiment" means that a particular feature, structure, or characteristic described in connection with the embodiment is included in at least one embodiment. Thus, the appearances of the phrases "in one embodiment" and "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure may be understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations and/or components are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various steps, which may be embodied in machine-executable instructions to be executed by a computer system. The computer system may comprise one or more general-purpose or special-purpose computers (or other electronic devices). Alternatively, the computer system may comprise hardware components that include specific logic for performing the steps or comprise a combination of hardware, software, and/or firmware. Without limitation, a computer system may comprise a workstation, desktop computer, laptop computer, disconnectable mobile computer, server, mainframe, cluster, so-called "network computer" or "thin client," tablet, smartphone, multimedia device, electronic reader, personal digital assistant or other hand-held computing device, "smart" consumer electronics device or appliance, or a combination thereof. A server may include a physical server, a server cluster, a distributed server, a virtual server, a cloud server, a computer providing resources to one or more clients, a combination of one or more of the aforementioned, and/or the like. Some or all of the functions, steps, and/or operations discussed herein may be performed by one or more clients and/or one or more servers. Those of skill in the art will realize possible divisions of operations between the one or more servers and the one or more clients.

Each computer system includes at least a processor and a memory; computer systems may also include various input devices and/or output devices. The processor may include one or more general-purpose central processing units (CPUs), graphic processing units (GPUs), or Digital Signal Processors (DSPs), such as Intel®, AMD®, ARM®, Nvidia®, ATI®, TI®, or other "off-the-shelf" microprocessors. The processor may include a special-purpose processing device, such as an ASIC, PAL, PLA, PLD, Field Programmable Gate Array (FPGA), or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light or other pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, memory card reader, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Embodiments may also be provided as a computer program product, including a non-transitory machine-readable storage medium having stored thereon instructions that may be used to program a computer system (or other electronic device) to perform processes described herein. The non-transitory machine-readable storage medium may include, but is not limited to, hard drives, floppy diskettes, optical disks, CD-ROMs, DVD-ROMs, ROMs, RAMs, EPROMs, EEPROMs, magnetic or optical cards, tapes, solid-state memory devices, or other types of media/machine-readable media suitable for storing electronic instructions.

Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies. One suitable network includes a server and several clients; other suitable networks may contain other combinations of servers, clients, and/or peer-to-peer nodes, and a given computer may function both as a client and as a server. Each network includes at least two computer systems, such as the server and/or clients.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" or wireless protocols known to those of skill in the art. The network may encompass smaller networks and/or be connectable to other networks through a gateway or similar mechanism.

Suitable software to assist in implementing the invention is readily provided by those of skill in the pertinent art(s) using the teachings presented here and programming languages and tools, such as Java, Pascal, C++, C, PHP, JavaScript, Python, C#, Perl, SQL, Ruby, Shell, Visual Basic, Assembly, Action Script, Objective C, Lisp, Scala, Tcl Haskell, Scheme, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer-executable code located within a memory device. A software module may, for instance, comprise one or more physical or logical blocks of computer instructions, which may be organized as a routine, a program, a script, an object, a component, a data structure, etc., that perform one or more tasks or implements particular abstract data types.

In certain embodiments, a particular software module may comprise disparate instructions stored in different locations of a memory device, different memory devices, or different computers, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that may be used according to the present invention is already available, such as general-purpose computers, computer programming tools and techniques, computer networks and networking technologies, and digital storage media.

FIG. 1 is a schematic diagram of a telepresence network 100 comprising a plurality of telepresence devices 130. A plurality of control devices 120, such as laptops, tablets, smart phones, and the like, may be configured to transmit video, audio, and/or commands to the telepresence devices 130 and receive video, audio, and/or measurement data from the telepresence devices 130. The control devices 120 may directly couple to the telepresence devices 130, and/or a server 110 may couple the control devices to the telepresence devices 130. In an embodiment, the server 110 may establish a connection between a control device 120 and a telepresence device 130, and the control device 120 and telepresence device 130 may communicate directly after the connection has been established. A connection between a control device 120 and a telepresence device 130 may be referred to as a session. The server 110 may comprise and/or be coupled to a hard drive 112. The hard drive 112 may be configured to store a history for one or more control devices 120 and/or telepresence devices 130. The history may include session data, commands, measurement data, recorded video and/or audio, annotations, bookmarks, and the like. The control devices 120 may be able retrieve the history from the hard drive 112 via the server 110. It should be understood that any processing required to be performed by the telepresence device 130, the control device 120, and/or the server 110 may be shared and/or distributed among the telepresence device 130, the control device 120, and/or the server 110 in any manner without departing from the scope of this disclosure. Accordingly, if the application states that the telepresence device 130 performs an action that requires execution by a processor, embodiments are contemplated where that action may be perform wholly or partially by the server 110 and/or the control device 120 even if not explicitly recited.

Figure 2:
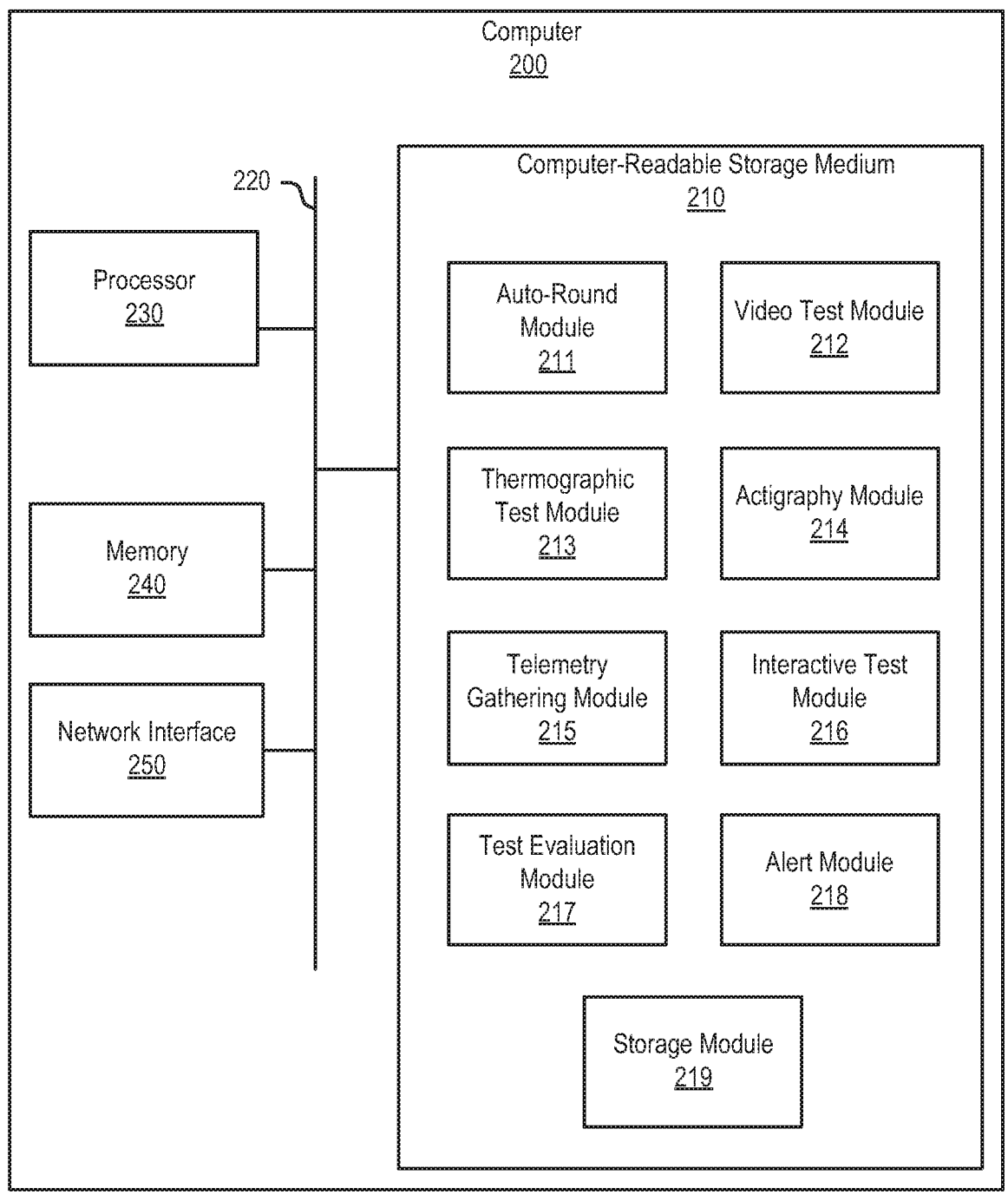
FIG. 2 is a schematic diagram of a computer configured to provide enhanced diagnostics by a telepresence device.

FIG. 2 is a schematic diagram of a computer 200 configured to provide enhanced diagnostics by a telepresence device. The computer 200 may include a processor 230 coupled to a volatile memory 240, a network interface 250, and a computer-readable storage medium 210 by a bus 220. In some embodiments, the computer-readable storage medium 210 may comprise the volatile memory 240. The computer-readable storage medium 210 may include a plurality of modules configured to perform specific functions. For example, an auto-round module 211 may be configured to cause the telepresence device to navigate to patients with a predetermined frequency to perform one or more tests; a video test module 212 may be configured to evaluate a characteristic of a patient based on video of the patient captured by an image sensor (e.g., using Eulerian video magnification); a thermographic test module 213 may be configured to evaluate a characteristic of the patient based on a thermographic image of the patient captured by a thermal camera; an actigraphy module 214 may be configured to determine a position of the patient and/or motion of the patient using data from a depth sensor and to determine a psychological state of the patient from the position and/or motion; a telemetry gathering module 215 may be configured to acquire telemetry data from a patient monitor, for example, using optical character recognition, by requesting the data from the patient monitor over a wireless network, by requesting the data from an electronic medical record system, and/or the like; an interactive test module 216 may be configured to perform a test requiring the patient to respond orally to one or more prompts and/or to perform one or more actions; a test evaluation module 217 may be configured to receive results from one or more tests and determine the existence of an adverse condition based on the results; an alert module 218 may be configured to notify one or more care providers of the adverse condition and to ensure a care provider responds to the alert; and a storage module 219 may be configured to store selected video, audio, and/or data. Alternatively, the computer 200 may contain more or fewer modules and/or a different computer may contain some of the modules.

Figure 3B:
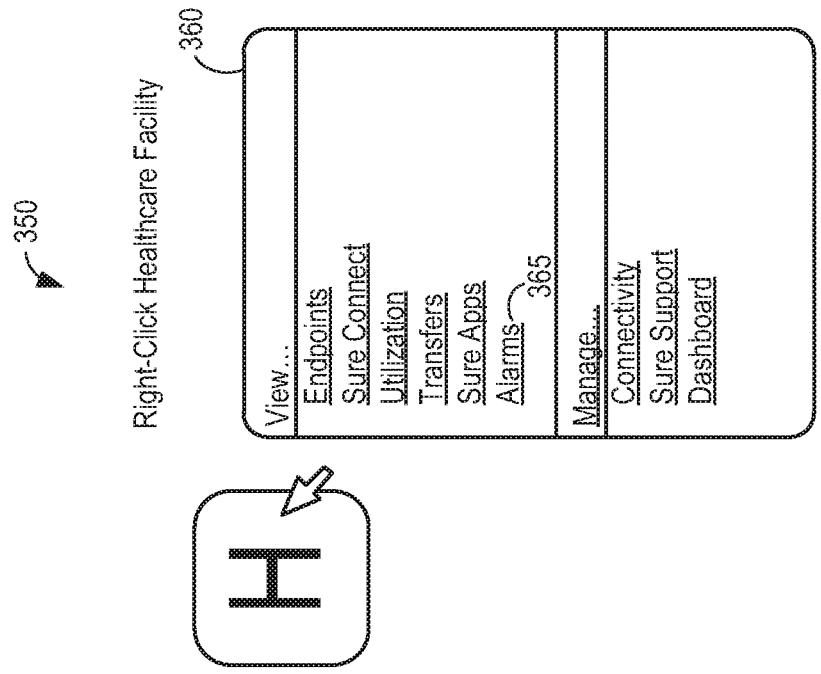
FIGS. 3A,B are exemplary screen displays that may be displayed to a user of a control device.
Figure 3A:
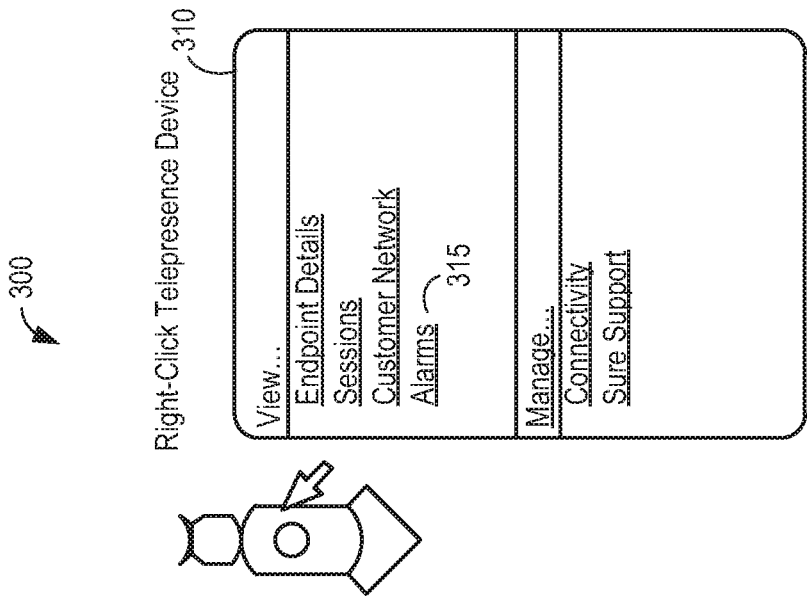

FIGS. 3A,B are exemplary screen displays 300, 350 that may be displayed to a user of a control device. The user may be attempting to connect to a telepresence device. A plurality of options 310, 360 may be displayed to the user including available endpoints to which the user may connect. The user may select the telepresence directly and/or select a healthcare facility or patient of interest. An optimal telepresence device may be automatically connected to if a healthcare facility or patient of interest is selected. The user may also be able to select an alarms option 315, 365 that allows a user to view telepresence devices that have triggered an alarm or healthcare facilities with patients for whom an alarm has been triggered. The alarms and/or additional patient data may allow the user to connect to telepresence devices near and/or interacting with patients most urgently needing attention. Once the user has connected to the telepresence device, the user may interact with a patient using audio, video, and/or data capabilities of the telepresence device. The user may develop a treatment plan and issue corresponding orders to local care providers and/or modify existing orders.

Figure 4:
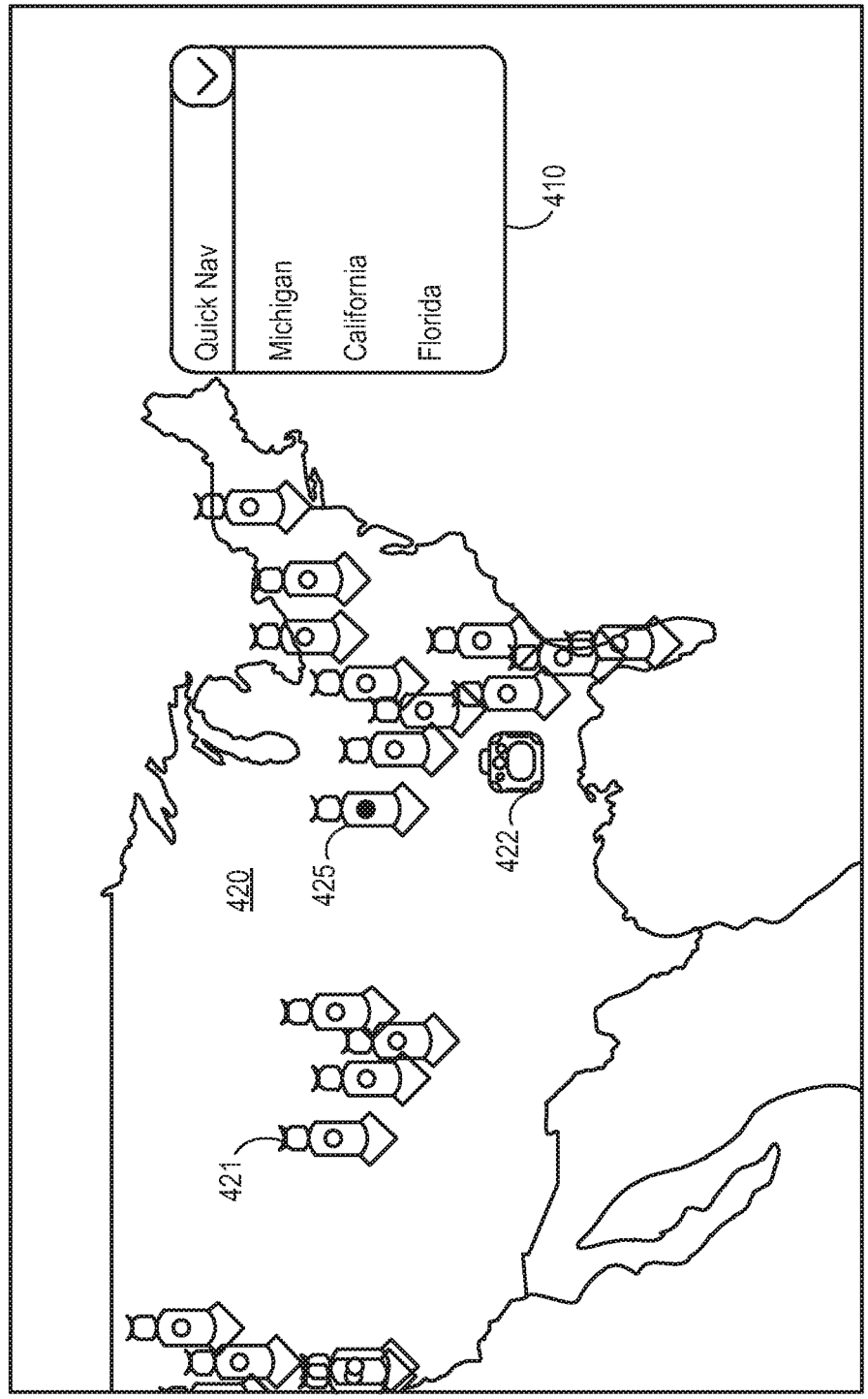
FIG. 4 is an exemplary screen display comprising a telepresence device location map.

FIG. 4 is an exemplary screen display 400 comprising a telepresence device location map 420. The locations of various telepresence devices 421, 422 may be illustrated as figures on the map 420. A Quick Nav bar 410 may allow the user to see telepresence devices available in a region of interest. The user may be able to connect to one of the telepresence devices 421, 422 by selecting the desired telepresence device from the map 420. A telepresence device 425 issuing an alarm may include a distinctive indication that an alarm is occurring. The distinctive indication may be configured to draw the attention of the user and may include a unique color, a flashing icon, text, a pop-up window, and/or the like. The user may select the alarming telepresence device 425 to connect to that telepresence device 425 and resolve the alarm.

Figure 5:
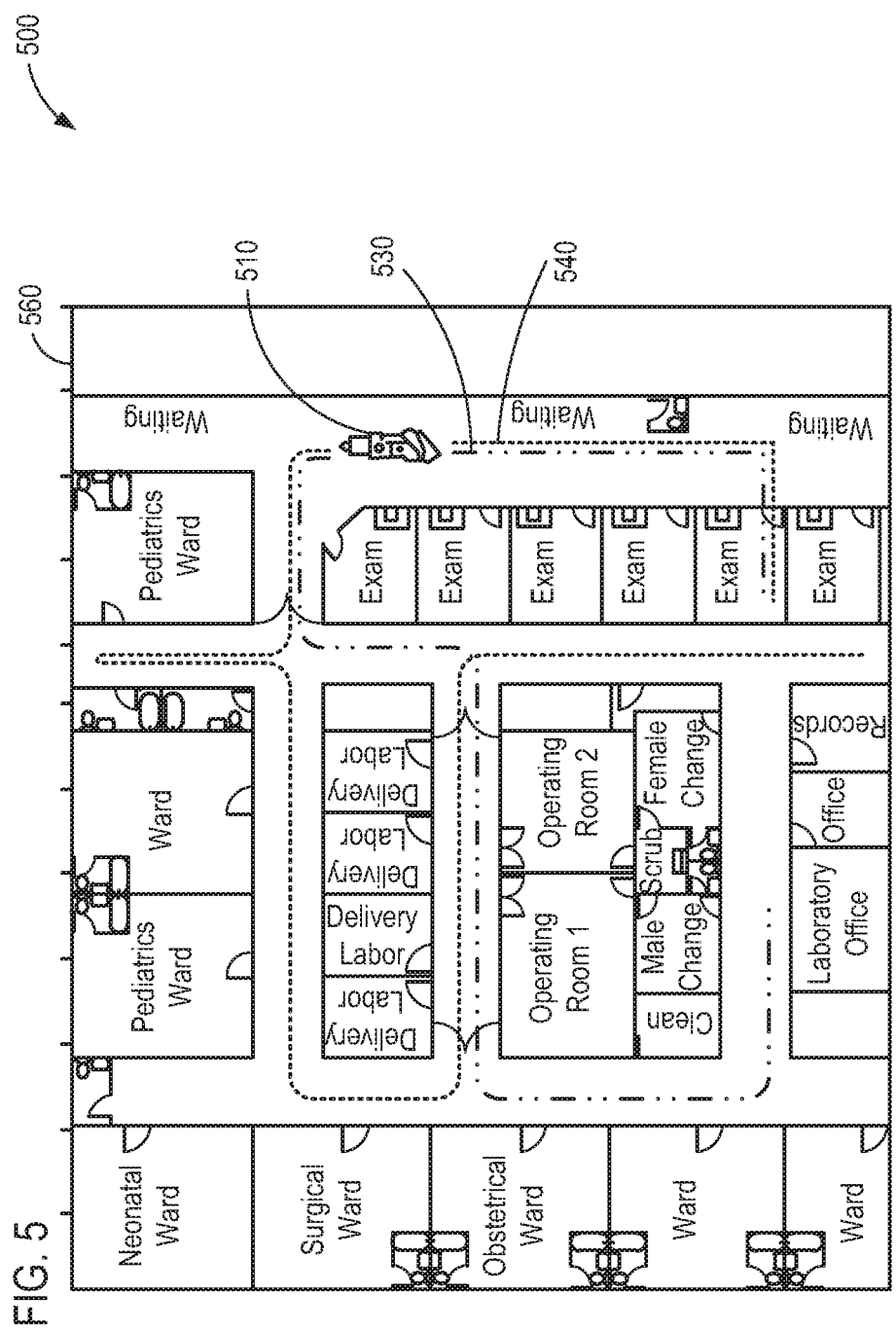
FIG. 5 is an exemplary depiction of a healthcare facility map.

FIG. 5 is an exemplary depiction 500 of a healthcare facility map 560. The healthcare facility map 560 and/or a digital representation of the map 560 may be used by a telepresence device 510 to autonomously navigate to a plurality of patients in turn to check the patients and evaluate whether each patient is experiencing a potentially harmful condition. The telepresence device 510 may perform one or more diagnostic activities to evaluate each patient. Diagnostic activities may include diagnostic tests, which may or may not require interaction by the patient, and may include gathering telemetry data from a source external to the telepresence device 510 (e.g., a patient monitor, an electronic medical records (EMR) system, etc.). The diagnostic activities may be specified in advance by a care provider and/or may be determined based on a previous diagnosis and/or previous results of diagnostic activities. The results of the one or more diagnostic activities may be processed by the telepresence device 510 and/or a computer system external to the telepresence device 510 (e.g., the server 110) to determine whether a potentially harmful condition exists with the patient.

In response to determining that a potentially harmful exists, the telepresence device 510 and/or the computer system may perform one or more actions responsive to the potentially harmful condition. The one or more actions may include archiving the results of the one or more diagnostic activities, alerting a local care provider, alerting a remote care provider, and/or the like. The action may be selected based on the severity of the potentially harmful condition, the probability the patient is experiencing the potentially harmful condition, and/or the like. Alternatively, or in addition, a user may have specified in advance what actions should be taken for particular results of the one or more diagnostic activities. If the action includes alerting a remote care provider, the telepresence device 510 may also prepare to receive a connection from the alerted remote care provider.

The telepresence device 510 may be able to receive medical data (e.g., a medical record of a patient) from a patient monitor, an EMR system, a telepresence network server (e.g., the server 110) and/or the like. The telepresence device 510 may also be able transmit medical data measured by the telepresence device 510, for example, to the EMR system for storage. The telepresence device 510 may transmit the medical data over a secure, wireless connection (e.g., a WiFi network) to the hospital's EMR and/or other databases, in some embodiments. Alternatively, or in addition, the telepresence device 510 may include local storage for persistent storage of the medical data measured by the telepresence device 510. The medical data may include instructions to the telepresence device 510 including diagnostic activities to perform, thresholds for evaluating the results of the diagnostic activities, a frequency of performing the diagnostic activities and/or checking the patient, actions to perform in response to the determinations of the evaluation of the results of the diagnostic activities, and/or the like. Alternatively, or in addition, the telepresence device 510 may determine diagnostic activities, evaluation thresholds, frequency of checking each patient, response actions, and/or the like by parsing the previous diagnoses and results of diagnostic activities indicated in the medical data.

The telepresence device 510 and/or the computer system may determine an order and/or a frequency for visiting the plurality of patients. For example, the telepresence device 510 may receive indications of a plurality of patients that it should routinely check and/or may include indications of patients that should be added or removed from the plurality of patients that the telepresence device 510 routinely checks. Any time there is a change in which patients are monitored by the telepresence device 510, the telepresence device 510 may redetermine the order and/or frequency for visiting the monitored patients. The frequency with which each patient needs to be checked may be specified by a care provider and/or included in medical data for each patient. Alternatively, or in addition, the telepresence device 510 and/or the computer system may determine a risk level for each patient and visit the higher risk patients more frequently than lower risk patients. The risk may be specified in the medical data, for example, as a numerical risk level, and/or the risk may be computed based on parsing of the medical data. The medical data may be parsed to detect risk factors (e.g., diagnoses requiring more frequency checking, physiological measurements correlated with higher risk, etc.).

In an embodiment, the telepresence device 510 may query the EMR system to ascertain whether a patient has been diagnosed (e.g., by a care provider, the telepresence device 510, and/or the like) with a urinary tract infection (UTI) or sepsis and may check the patient more frequently for sepsis if the patient has a UTI and/or an existing sepsis diagnosis due to the higher risk for sepsis. Because it can be important to achieve certain metrics (e.g., venous pressure, hemoglobin levels, etc.) in a short time frame when treating sepsis, the telepresence device 510 may also, or instead, monitor sepsis patients at a predetermined frequency (e.g., at predetermined intervals) to ensure that they are meeting the desired goals and/or that care providers know when a patient characteristic is outside a desired range. Alternatively, or in addition, a care provider may manually identify patients having a higher risk of sepsis (e.g., in an online database that can be queried by the telepresence device 510).

The exemplary depiction 500 of the healthcare facility map 560 includes a previously travelled route 540 and a route 530 currently being travelled by the telepresence device 510. In the illustrated embodiment, the telepresence device 510 does not simply visit the rooms in an order determined based on spatial proximity to each other. Rather, the telepresence device 510 may weight the relative spatial proximity in addition to weighting patient monitoring frequency, which may have been determined based on risk. The telepresence device 510 may attempt to take advantage of spatial proximity of patients while also ensuring that higher risk patients aren't neglected for lower risk patients that are more proximate. In some embodiments, movement of the telepresence device 510 may be controlled by a central server (e.g., the server 110), which may receive real-time telemetry data from a plurality of patients and dynamically adjust the order of patient monitoring, and/or the telepresence device 510 may configured to receive real-time telemetry data and dynamically adjust its route.

Figure 6:
FIG. 6 is a perspective view of a telepresence device performing one or more diagnostic activities on a patient using an image sensor.

FIG. 6 is a perspective view of a telepresence device 610 performing one or more diagnostic activities on a patient 650 using an image sensor 611. The telepresence device 610 may include the image sensor 611 (e.g., a video camera) and a display device 615, which is showing an image captured by the image sensor 611 in the illustrated embodiment. In many embodiments, the image captured by the image sensor may not be displayed on the display device 615 but is included here for illustrative purposes. Instead, the image may be processed internally by the telepresence device 610, provided to a remote care provider, archived, etc. The telepresence device 610 may use the image sensor 611 to measure one or more patient characteristics, such as a physiological characteristic, of the patient 650. For example, the telepresence device 610 may use Eulerian video magnification to detect small changes in color and/or small movements in the captured video and amplify the detected changes and/or movements. The telepresence device 610 may then extract heart rate from detected changes in skin color (e.g., by determining the frequency of skin reddening corresponding to heart beats) and/or respiration rate from detected movements of the patient's chest (e.g., by determining the frequency of chest movements).

Alternatively, or in addition, the telepresence device 610 may determine a measurement of a physiological characteristic by receiving telemetry data from a patient monitor 630. In one embodiment, the telepresence device 610 may use optical character recognition to read telemetry data displayed by the patient monitor 630. In another embodiment, the telepresence device 610 may use a wireless network to request the telemetry data from the patient monitor 630 and/or to request the telemetry data from a computer system coupled to the patient monitor 630 (e.g., an EMR system).

Figure 7:
FIG. 7 is a perspective view of the telepresence device performing one or more diagnostic activities on a fluid bag using the image sensor.

The telepresence device 610 may also, or instead, detect the patient's pallor using the image sensor 611. Referring also to FIG. 7, the telepresence device 610 may be configured to determine the fluid level, the fluid color, and/or the like of a fluid bag 730 of a patient 750 using the image sensor 611. For example, the telepresence device 610 may detect when intravenously supplied saline, medication, and/or the like is running low, and/or the telepresence device 610 may detect the color and/or fluid level of a urine bag (e.g., to detect perfusion). If a potentially harmful condition is determined to exist from the one or more diagnostic activities, an alarm may be triggered. In an embodiment, the patient monitor 630 and/or fluid bag 730 may be identified using scale-invariant feature transform (SIFT), speeded up robust features (SURF), and/or oriented features from accelerated segment test and rotated binary robust independent elementary features (ORB). The boundaries of the patient's face may be determined using Haar feature detectors. A level of the fluid bag 730 may be determined by finding the most salient line using Hough line detection. Color thresholds may be determined by averaging the color within the boundary of the fluid bag 730 or facial area and calculating the RGB distance of that color to a desired norm. The system may perform white balancing with a known white feature in the room prior to performing a test requiring color measurement since white balance may materially impact color detection.

The measurements of the patient characteristics may complement the telemetry data received from the patient monitor 630, and/or the measurements may back up or replace the telemetry data. For example, pallor, fluid level, fluid color, temperature symmetry (as discussed below with regard to FIG. 8) and/or the like may be combined with telemetry data to evaluate whether a potentially harmful condition exists. Alternatively, or in addition, the telemetry data may correspond to the one or more patient characteristic measured by the telepresence device 610. The telepresence device 610 may measure the one or more patient characteristics to confirm accuracy of the telemetry data, and/or the telepresence device 610 may measure the one or more patient characteristics once it has attempted to acquire the telemetry data and has been unable to do so (e.g., the telepresence device 610 detects that the patient 650, 750 is not connected to a patient monitor, requests telemetry data and does not receive a response, determines the patient is in room with little or no telemetry or unlikely to have telemetry, such as a room in a Medical/Surgical ward, and/or the like).

If a potentially harmful condition is detected, an action responsive to the potentially harmful condition may be performed as previously discussed. The action may include providing medical data acquired by the image sensor 611 to a local and/or remote care provider. For example, images and/or video of fluid levels, fluid color, pallor, etc. may be made available to the care provider (e.g., by uploading over a wireless network to a central server), and/or an indication of why the fluid level, fluid color, pallor, etc. caused an alarm to be triggered may be provided. For some alarms, such as when a patient potentially has sepsis, a care provider may want to watch for visual cues of respiratory distress when making a diagnosis. Accordingly, the telepresence device 610 may record a video clip of the patient's respiration once the alarm has been triggered and while waiting for the care provider to respond. The video clip may be made immediately available to the care provider once the care provider has responded. For other potentially harmful conditions, video clips of other activities by the patient and/or other regions of the patient's body may be captured instead.

Figure 8:
FIG. 8 is a perspective view of a telepresence device performing one or more diagnostic activities on a patient using a thermal camera.

FIG. 8 is a perspective view of a telepresence device 810 performing one or more diagnostic activities on a patient 850 using a thermal camera 812. The telepresence device 810 may include a display device 815, which is showing a thermographic image captured by the thermal camera 812 in the illustrated embodiment. In many embodiments, the thermographic image may not be displayed on the display device 815 but is included here for illustrative purposes. Instead, the image may be processed internally by the telepresence device 810, provided to a remote care provider, archived, etc. The telepresence device 810 may estimate a temperature of the patient 850 from the thermographic image, for example, if the temperature cannot be determined from telemetry data. The telepresence device 810 may use Haar feature detectors to detect the boundaries of the face and compute an average temperature within those boundaries. The telepresence device 810 may determine an overall or core temperature and/or may determine whether the patient's limbs/extremities are warmer or colder than is desirable relative to the overall or core temperature. The telepresence device 810 may determine the location of limbs using a depth sensor (not shown) and associated skeletal mapping software. The temperature of the limb may then be determined by computing an average temperature of an area in close proximity to the center point of the detected limb. The patient may be prompted to remove part of a blanket to facilitate this measurement. Alternatively, or in addition, the telepresence device 810 may determine whether the temperature of the patient 850 is asymmetric (e.g., whether limbs on one side of the body are warmer or colder than the other side). The telepresence device 810 may also determine whether torso temperature is asymmetric. To do so, the telepresence device 810 may perform skeletal mapping to calculate a center line of the patient's body and may compare temperatures to the left and right of the center line (e.g., points 2, 4, 6, or 8 inches to each side of the center line).

Patient thermal data may be particularly helpful in detecting certain potentially harmful conditions, such as sepsis or infection, that can lead to mortality if not detected early enough. In general, patient thermal data may be used to detect high fever by observing overall temperature, to assess local hot spots suggestive of inflammation or infection, to detect asymmetric body temperature abnormalities, to detect symmetric body temperature abnormalities (e.g., warm shock vs. cold shock), and/or the like. For example, sepsis may be associated with a gradually rising temperature and/or high overall temperature, thermal asymmetry, a gradually rising heart rate, and respiratory distress. For patients at risk for sepsis and/or who begin to show signs, the telepresence device 810 may check the patient on a strict schedule. Because some indications of sepsis include gradual trends, the telepresence device 810 may store (e.g., locally, on an EMR system, etc.) one or more pieces of patient data (e.g., thermal data, telemetry data, etc.) for later review by the telepresence device 810 and/or a care provider. Similarly, patient data may be stored during management and/or treatment of sepsis to detect progress and/or to detect, manage, and/or treat one or more other predetermined conditions.

To detect sepsis, the telepresence device 810 may attempt to measure patient characteristics facially indicative of sepsis and evaluate measurements of patient characteristics relative to historical measurements to detect trends indicative of sepsis. In an embodiment, the telepresence device 810 may monitor for an overall temperature over 100 degrees Fahrenheit, a temperature rise of over 2% or 2 degrees Fahrenheit in two hours, a heart rate rise of over 20%, and/or the like. If an individual characteristic and/or plurality of characteristics are indicative of sepsis, the telepresence device 810 may take responsive action including triggering an alarm, paging a designated specialist, preparing for connection by an off-site specialist, physically locating a local care provider (as discussed below with regard to FIG. 12), and/or the like. The telepresence device 810 and/or a central server (not shown) may perform responsive actions according to a prioritize ordering. The telepresence device 810 may query a database to determine if a local qualified care provider is available, in which case the local qualified care provider may be paged. Otherwise, if a local qualified care provider is not available, a remote qualified care provider who is on-call may be paged, and the telepresence device 810 may prepare for a remote connection. Heart rate and respiration rate may be measured directly by the telepresence device 810 (e.g., using Eulerian video magnification) and/or may be determined by receiving telemetry data. In some embodiments, the telepresence device 810 may trigger a sepsis alarm only if there are a combination of multiple indications, such as one or more indications from a networked telemetry device along with one or more indications from the telepresence device's own imaging systems.

Figure 9:
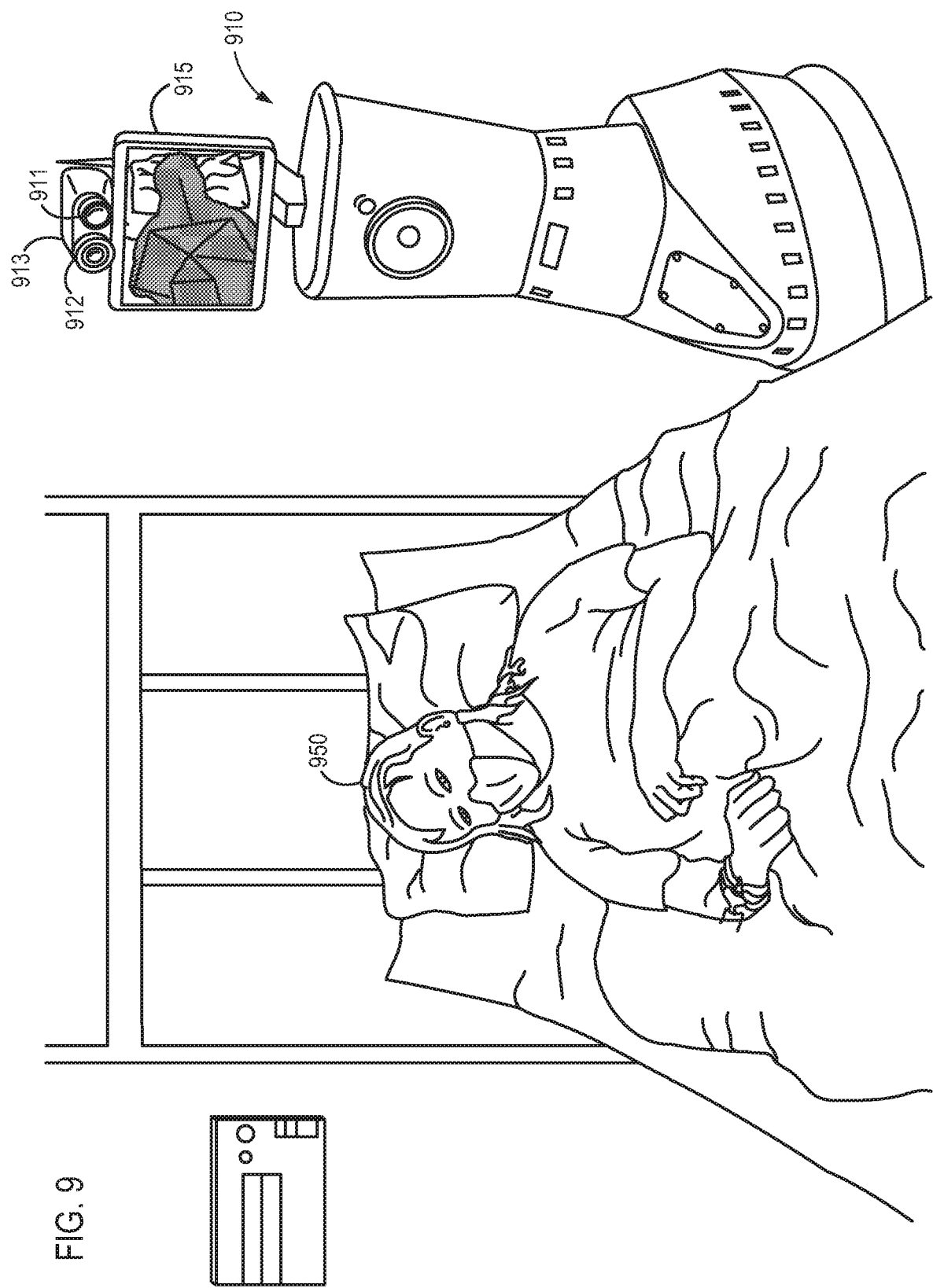
FIG. 9 is a perspective view of a telepresence device performing one or more diagnostic activities on a patient using a depth sensor.

FIG. 9 is a perspective view of a telepresence device 910 performing one or more diagnostic activities on a patient 950 using a depth sensor 913. The telepresence device 910 may include one or more image sensors 911 (e.g., a video camera) used by the depth sensor 913 to determine depth. Alternatively, or in addition, the one or more image sensors 911 used by the telepresence device 910 may be distinct from image sensors used by the telepresence device 910 to perform visual assessments. The telepresence device 910 may also include a display device 915, which is showing a stick model of the patient 950 as determined by the depth sensor in the illustrated embodiment. In many embodiments, the internal depth model may not be displayed on the display device 915 but is included here for illustrative purposes. Instead, the model may be processed internally by the telepresence device 910, provided to a remote care provider, archived, etc. The position of the patient 950 and/or the patient's limbs and motion by the patient 950 may be determined using the depth sensor (e.g., via an off-the-shelf skeletal mapping software program configured to process the 3D point cloud data from the depth sensor). The depth sensor 913 may be used in combination with a thermal camera 912 to detect the existence of thermal asymmetries. For example, the depth sensor 913 may determine the location of one or more limbs, and the temperature of the limb may be determined from temperature data corresponding to the location of the limb.

The telepresence device 910 may be able to determine whether the patient is sleeping based on gross motor activity of one or more of the patient's body parts (e.g., the telepresence device 910 may perform actigraphy using the depth sensor 913). Monitoring multiple body parts may improve the accuracy of the determination of whether the patient is sleeping. In an embodiment, the system may detect motion of limbs using skeletal mapping with the depth sensor, may detect motion of the head using Haar feature detectors, and may identify a sleeping state versus wakefulness through preconfigured thresholds of movement of the limbs and face.

The telepresence device 910 and/or local care providers may be able to shift interactive tests and/or diagnostics to times when the patient 950 is awake based on the assessment by the telepresence device 910 of whether the patient 950 is asleep. For example, a local care provider may subscribe to be notified by the telepresence device 910 when the patient 950 wakes up. Once the patient 950 is awake, any delayed tests may be performed. Because patients will need to be woken up less frequently, the stress, fatigue, and "ICU psychosis" that may result from frequent waking can be avoided. Sleep may be one of several psychological states detectable by the telepresence device 910. The telepresence device 910 may also or instead be configured to detect agitation and/or distress in the patient based on the position and/or motion of the patient's limbs (e.g., using a modification of the thresholds for detecting a sleeping state). An alarm may be triggered by the telepresence device 910 if agitation or distress is detected without any other indications of a potentially harmful condition and/or if agitation and/or distress are detected in combination with one or more patient characteristics indicative of a potentially harmful condition.

Figure 10:
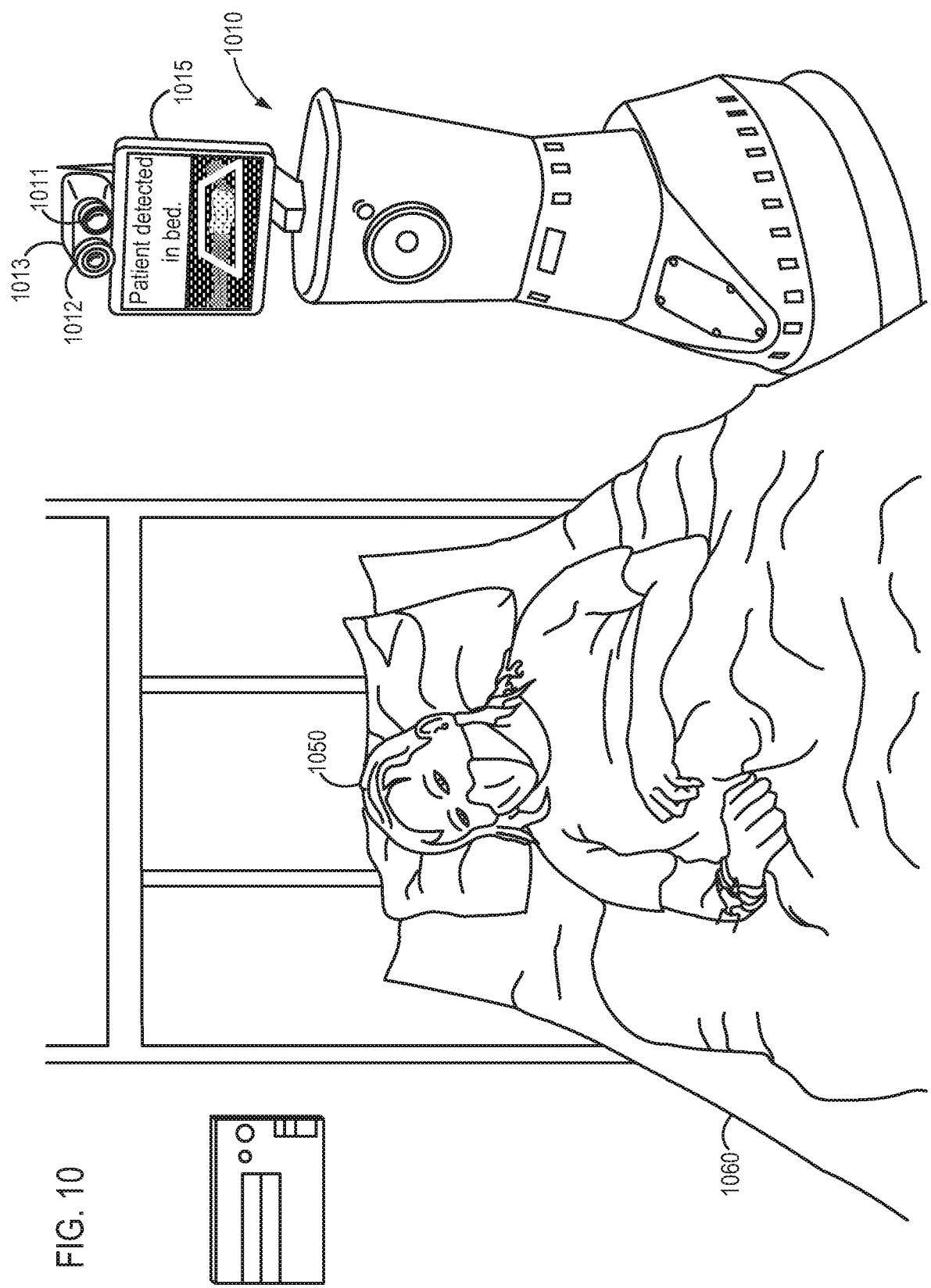
FIG. 10 is a perspective view of a telepresence device evaluating whether a patient is currently in their bed.

FIG. 10 is a perspective view of a telepresence device 1010 evaluating whether a patient 1050 is currently in their bed 1060 or, for example, has fallen out. The telepresence device 1010 may include one or more image sensors 1011 (e.g., a video camera), a thermal camera 1012, a depth sensor 1013, which may leverage the one or more image sensors 1011 to determine depth, and/or the like. The telepresence device 1010 may also include a display device 1015, which is indicating that the patient 1050 has been detected in the bed 1060 in the illustrated embodiment. In many embodiments, the determination of whether the patient 1050 is in the bed 1060 may not be displayed on the display device 1015 but is included here for illustrative purposes. Instead, sensor data may be processed internally by the telepresence device 1010, provided to a remote care provider, archived, etc. The telepresence device 1010 may use a combination of information from the one or more image sensors 1011, the thermal camera 1012, the depth sensor 1013, and/or the like to detect whether the patient 1050 is in their bed 1060. For example, the telepresence device 1010 may detect the edges of the bed 1060 using the depth sensor 1013 and/or the one or more image sensors 1011 and may determine the location of the patient 1050 using the thermal camera 1012 and/or the depth sensor 1013. If the patient location is inside the detected edges, the telepresence device 1010 may conclude the patient 1050 is in the bed 1060. If the patient location is not inside the detected edges and/or only partially inside the detected edges, the telepresence device 1010 may conclude the patient 1050 is out of the bed 1060 and/or has fallen. The telepresence device 1010 may take a responsive action, such as triggering an alarm if the patient 1050 is out of the bed 1060.

Figure 11:
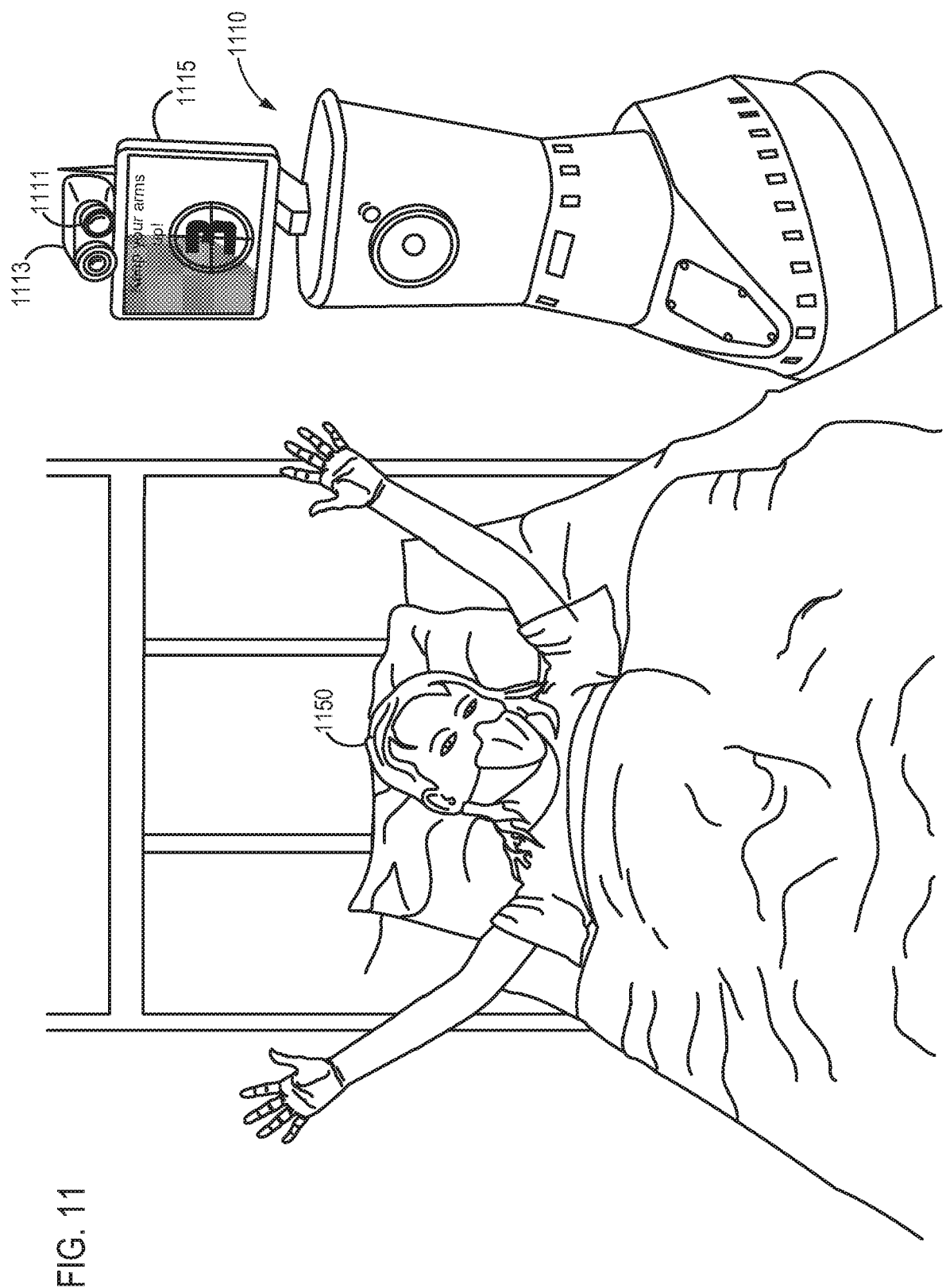
FIG. 11 is a perspective view of a telepresence device performing an interactive test with a patient.

FIG. 11 is a perspective view of a telepresence device 1110 performing an interactive test with a patient 1150. The telepresence device 1110 may display instructions to the patient 1150 using a display device 1115 and/or may speak instructions using one or more speakers (not shown). The interactive test may require the patient 1150 to correctly perform an action. The telepresence device 1110 may determine the performance of the patient 1150 using one or more image sensors 1111, a depth sensor 1113 in combination with skeletal mapping software, which may leverage the one or more image sensors 1111, speech recognition, telemetry data, and/or the like. The telepresence device 1110 may evaluate the performance of the patient 1150 and determine whether a potentially harmful condition exists and/or a responsive action should be taken.

For example, the telepresence device 1110 may evaluate whether the patient 1150 has suffered a stroke using the National Institute of Health Stroke Scale (NIHSS). The telepresence device 1110 may explain the NIHSS using audio and/or graphics, video, text, etc. Instructions for each test in the NIHSS may be displayed on the display device 1115 and/or played using the one or more speakers. To determine responsiveness (NIHSS #1A), the telepresence device 1110 may provide an audio and/or video stimulus to the patient 1150 and use the depth sensor 1113 to detect the patient's response to the stimulus. The telepresence device 1110 may present a prompt, such as an audio questions or an image (e.g., pictures, text, etc.), to the patient 1150 and use speech recognition to evaluate responses to determine consciousness, detect aphasia, detect dysarthria, and/or the like (NIHSS #1 B, 9, and 10). Allowances may be made for false positives and/or false negatives that may result from errors in speech recognition. Alternatively, or in addition, responses may be recorded for evaluation by a care provider. Facial recognition (e.g., using Haar-like feature analysis and/or the like via the image sensor 1111) may be used to detect facial symmetry and/or expression to determine the patient's ability to close her eyes and/or facial palsy (NIHSS #1C and 4). Eye tracking and/or movements detected by the depth sensor 1113 may be used to determine patient responsiveness to commands (e.g., video and/or audio commands), determine gaze palsy, determine hemianopia, and/or the like (NIHSS #1C, 2, and 3).

Arm drift, leg drift, and limb ataxia may be detected using the depth sensor 1113, and the display device 1115 may provide instructions and/or a countdown timer to the patient 1150 during the test (NIHSS #5, 6, and 7). For example, the telepresence device 1110 may play synthesized speech stating, "Could you please sit up and hold your arms directly in front of you while you see the timer on my screen? Thank you." The telepresence device 1110 may then evaluate whether the patient is able to maintain their limbs in an elevated position for a predetermined amount of time. In some embodiments, the telepresence device 1110 may be equipped to provide a tactile stimulus necessary to detect sensory loss and/or extinction and may use speech recognition to determine whether the patient properly perceives the tactile stimulus (NIHSS #8, 11). The telepresence device 1110 may compute a score on the NIHSS to evaluate the patient's performance and determine whether the patient 1150 has suffered a stroke. Alternatively, or in addition, the telepresence device 1110 may be unable to perform one or more tests and may determine a score without the one or more unperformed tests and/or may request that care provider perform the one or more unperformed tests. The results of the tests, which may include video recording of the test, may be made instantly available to local and/or remote care providers. An alarm may be triggered if certain stroke scale factors or a combination of factors fall outside of certain thresholds. Recorded video, audio, and/or still images for some or all tests may be stored locally and/or on a remote storage device by the telepresence device 1110 for later review by a care provider and/or for quality assessment.

The telepresence device 1110 may directly ask the patient 1150 to assess her own condition. For example, the telepresence device 1110 may ask the patient "How are you breathing?"; "On a scale of 0 to 10, how much pain are you feeling right now?"; and/or the like. To help avoid falling incidents, which frequently occur when patients attempt to use the bathroom, the telepresence device 1110 may ask patients whether they need to use the bathroom. Prompting the patients may be necessary because of embarrassment and/or a lack of lucidity on the part of the patients. The telepresence device 1110 may use speech recognition to determine the response of the patient 1150. The responses may be archived in audio and/or text form, and/or the telepresence device 1110 may perform a responsive action if it determines one is necessary, for example, by sending an alert to the nursing station that the patient requires assistance in walking to the bathroom. Additionally, the telepresence device 1110 may be able to request that the patient 1150 remove blankets from a part of their body in order to analyze it thermally since blankets may decrease accuracy of thermal imaging.

Delirium may be associated with increased risk of mortality due to overdosing. Thus, the telepresence device 1110 may perform one or more interactive tests to detect delirium and/or the level of sedation (e.g., using the Richmond Agitation Sedation Scale). If the patient 1150 is in danger of overdosing, the telepresence device 1110 may take a responsive action, such as sending a recommendation to one or more care providers to stop or reduce medication to the patient 1150, noting that a change in medication may be needed in the patient's health record or another documentation system, triggering an alarm, and/or the like. The telepresence device 1110 may determine a frequency of sedation and/or delirium testing based on a risk for overdose and/or an amount of medication previously received and/or currently being received.

Figure 12:
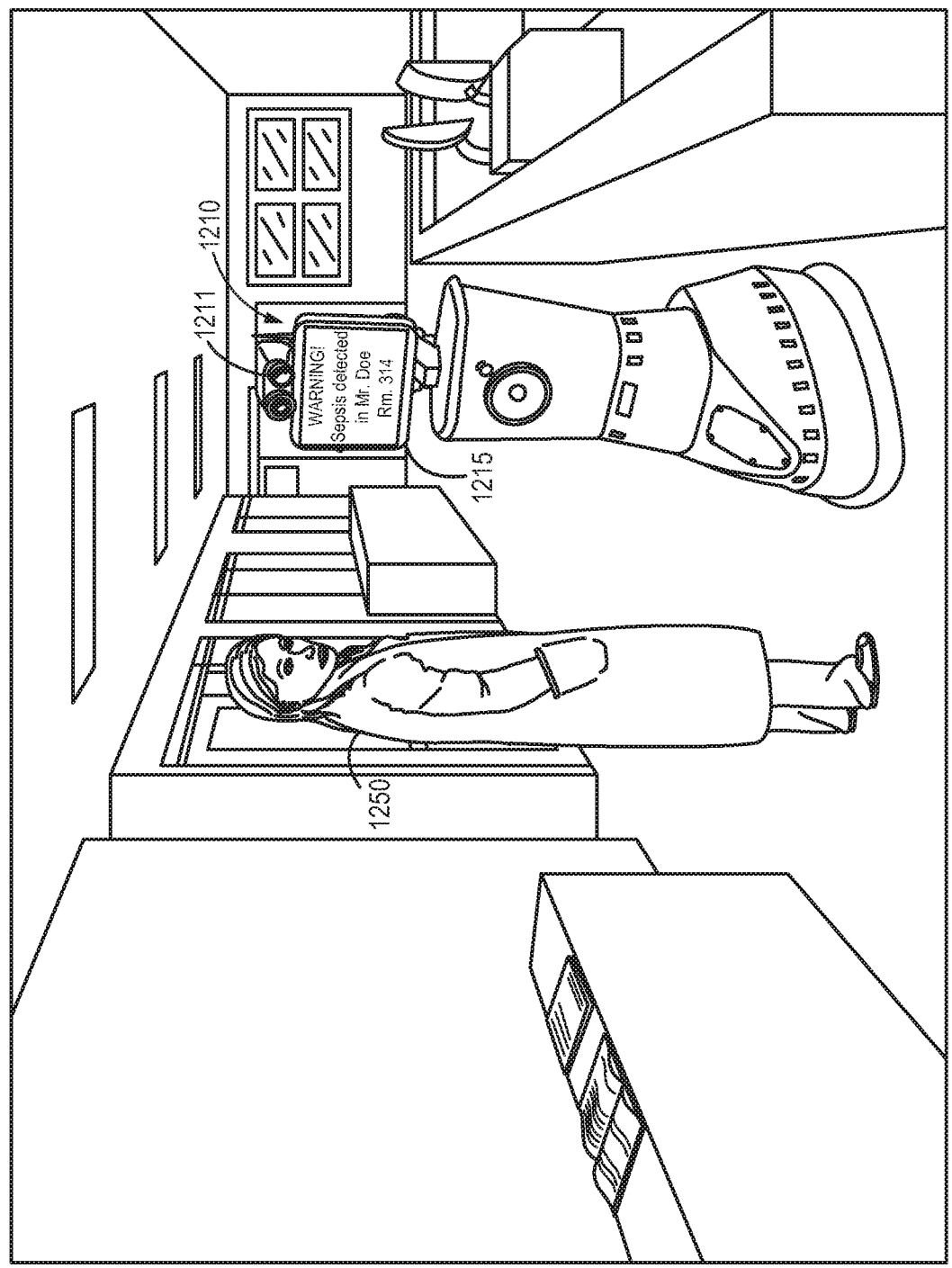
FIG. 12 is a perspective view of a telepresence device informing a care provider in-person of the existence of an alarm.

FIG. 12 is a perspective view of a telepresence device 1210 informing a care provider 1250 in-person of the existence of an alarm. Care providers may suffer alarm fatigue and may not respond to alarms, for example, under the belief the alarms are not true emergencies. When an alarm has been triggered for a patient, the telepresence device 1210 may locate a care provider 1250 by navigating to a nurses' station as identified on an internal map and identifying a care provider 1250 through Haar feature face detection at a predetermined depth behind the counter. The telepresence device 1210 may alert the identified care provider 1250 that the patient is experiencing an alarm. In some embodiments, the telepresence device 1210 may only travel to the care provider 1250 if the alarm indicates the patient is experiencing a high-priority condition and/or if a predetermined amount of time has transpired without the arrival of a care provider 1250.

The telepresence device 1210 may have triggered the alarm (e.g., after performing one or more diagnostic activities) and/or may determine that an alarm has already been triggered (e.g., by receiving an indication from a patient monitor, an EMR system, and/or the like). Similarly, the telepresence device 1210 may locate the care provider 1250 (e.g., using a vision system 1211), and/or the telepresence device 1210 may be informed of the nearest care provider 1250 by a hospital computer system, which may localize staff through RFID tags in the care providers' badges. The telepresence device 1210 may alert the care provider 1250 by displaying a message on a display device 1215, by playing an alert sound, by playing an audio message comprising synthesized and/or prerecorded speech, and/or the like. The telepresence device 1210 may be configured to increase volume and/or become increasingly annoying until the care provider responds.

A telepresence device may be configured to determine diagnostic activities, responsive actions, and/or frequency of monitoring based on a patient's medical condition, past diagnostic results, etc., for example, as indicated by patient data received by the telepresence device. Alternatively, or in addition, care providers may be able to create custom protocols for monitoring specific patients and/or specific medical conditions, such as a custom protocol for a patient who just underwent a revascularization procedure. Custom protocols may be saved as presets that can be reused. The care provider may be able to include in the custom protocol some or all of the diagnostic activities and/or responsive actions that the telepresence device and/or a ward's telemetry system is able to perform, such as those previously discussed. The care provider may select a predetermined and/or custom frequency of monitoring. The care provider may be able specify predetermined and/or custom thresholds for diagnostic activities. The custom protocol may include threshold for single measurements and/or trending thresholds as determined from a local storage device, an EMR system, and/or the like.

The responsive actions may include alerting a care provider. The protocol may specify which care providers are alerted and how they are alerted. The protocol may specify whether a nurse or doctor should be contacted, which specialty should be contacted, whether a local or remote care provider should be contacted, and/or the like. For example, a custom protocol may specify that a cardiologist should be contacted for a blood flow anomaly and a neurologist should be contacted for motor response deficiencies. The protocol may specify that a text message should be sent, a page should be sent, an alarm should be triggered, an in-person notification should be delivered, and/or the like. Other responsive actions, such as archiving patient data, preparing to receive a remote connection, etc., may be performed as well or instead. The archived patient data may be available for later review by the telepresence device, a local and/or remote care provider, and/or the like. Table 1 is an exemplary partial list of drop-down options available for custom protocols and includes diagnostic activities and responses that a telepresence device may perform in an embodiment:

| Existing Telemetry (or thermal or Eulerian) | |
| --- | --- |
| V1 | Heart rate |
| V2 | Breathing rate |
| V3 | Gross Temperature |
| Patient Q&A (speech recognition) | |
| Q1 | Magnitude of pain [specify region]: respond 1 to 10 |
| Q2 | Stroke scale #5, #6, and #7 (via 3D point cloud/skeletal mapping) |
| Q3 | Stroke scale #1b, #9, and #10 (via speech recognition) |
| Q4 | Stroke scale #2 and #3 (via gaze tracking) |
| Thermal & Intelligent Imaging | |
| T1 | Extremity temperature |
| T2 | Asymmetry of temperature |
| T3 | Fluid Color |
| Actions: Notifications/Warnings/Archiving | |
| A1 | Notify RN immediately |
| A2 | Notify remote intensivist on call |
| A3 | Notify RN when round complete |
| A4 | Archive image/data |
| A5 | Notify remote cardiologist |
| A6 | Notify remote neurologist |
| Frequency of Monitoring | |
| F1 | q-15-min × __ hours |
| F2 | q-30-min × __ hours |
| ... | |
| F8 | q-8-hrs × __ hours |

Table 2 includes examples of custom protocols that may have been specified by a care provider (e.g., using a preset, for one-time use for a specific patient, etc.) and/or performed by a telepresence device:

| Patient # | Freq. | Optional custom name or reminder | Sensor 1 | Test 1 | Responses | |
|---|---|---|---|---|---|---|
| 15432 | F4 | Monitor for chest pain/increase | Q1 [chest] | >5 or increase | A1 | A2 |
| 18723 | F7 | Warmth of extremity after revascularization | T1 [Arm-Left-Upper] | 2 deg drop from baseline | A3 | A6 |
| 17892 | F4 | Warmth of extremity with IAPD present | T1 [Leg-Right] | >48 C. | A2 | A4 |
| 14998 | F2 | Breathing pattern with COPD exacerbation | V2 | >40 | A1 | A2 |
| 17894 | F4 | Urine output monitoring for perfusion | T3 [Urine-Bag] | color<>RGB_urine_norm | A1 | A2 |
| 18023 | F7 | Neuro-motor/ataxia | Q2 | score not_in NIHSS_norm | A6 | A1 |
| 19001 | F7 | Neuro-LOC/language | Q3 | score not_in NIHSS_norm | A6 | A1 |
| 18987 | F6 | Neuro-gaze/visual | Q4 | score not_in NIHSS_norm | A6 | A1 |

The telepresence device may continue to perform each custom protocol at the designated frequency until that custom protocol is removed, until it is detected that the patient has been discharged, and/or the like.

According to various embodiments, a telepresence and/or control device may be configured with all or some of the features and embodiments described herein. For example, a telepresence and/or control device may include any number of the features and embodiments described herein as selectively displayed and/or selectively functional options. An explicit enumeration of all possible permutations of the various embodiments is not included herein; however, it will be apparent to one of skill in the art that any of the variously described embodiments may be selectively utilized, if not at the same time, in a single telepresence and/or control device.

It will be understood by those having skill in the art that many changes may be made to the details of the above-described embodiments without departing from the underlying principles of the disclosure. The scope of the present disclosure should, therefore, be determined only by the following claims.

The invention claimed is:

1. A telepresence system, comprising:
a telepresence device coupled to a network, the telepresence device including a camera that captures video in a vicinity of a patient, a monitor that displays the video, a microphone, and a speaker, wherein the telepresence device analyzes the video to determine a color and a fluid level of a fluid bag in the video;
a control device coupled to the network, the control device including a camera, a monitor, a microphone, and a speaker; and
a server coupled to the network, the server is configured to establish a session between the control device and the telepresence device, wherein during the session, the control device monitor displays video captured by the camera of the telepresence device and the telepresence device monitor displays video captured by the control device camera, and wherein the determined color and fluid level are transmitted to the server and stored in an electronic medical record, and wherein the server is configured to control a movement of the telepresence device and trigger an alarm when the determined color of the fluid bag deviates from a predetermined norm.

2. The system of claim 1, wherein the system uses Eulerian video magnification to detect a change in color in the video.

3. The system of claim 2, wherein the system measures a heart rate of the patient from the detected change in color.

4. The system of claim 1, wherein the system uses Eulerian video magnification to detect a movement in the video.

5. The system of claim 4, wherein the system measures a respiration rate of the patient from the detected movement.

6. The system of claim 1, wherein the system measures a pallor of the patient using the video.

7. The system of claim 1, wherein the system measures a body temperature of the patient using a thermal camera coupled to the telepresence device.

* * * * *